United States Patent
Zheng et al.

(10) Patent No.: US 9,867,579 B2
(45) Date of Patent: Jan. 16, 2018

(54) METHOD OF ASSISTING MONITORING ALARM AND MEDICAL EXTERNAL EQUIPMENT USING THE SAME

(71) Applicant: Edan Instruments, Inc., Shenzhen, Guangdong (CN)

(72) Inventors: Ruhai Zheng, Guangdong (CN); Aijun Chen, Guangdong (CN)

(73) Assignee: Edan Instruments, Inc., Shenzhen, Guangdong (CN)

( * ) Notice: Subject to any disclaimer, the term of this patent is extended or adjusted under 35 U.S.C. 154(b) by 0 days.

(21) Appl. No.: 15/039,879

(22) PCT Filed: Dec. 24, 2013

(86) PCT No.: PCT/CN2013/090292
§ 371 (c)(1),
(2) Date: May 27, 2016

(87) PCT Pub. No.: WO2015/078074
PCT Pub. Date: Jun. 4, 2015

(65) Prior Publication Data
US 2016/0374627 A1    Dec. 29, 2016

(30) Foreign Application Priority Data
Nov. 29, 2013    (CN) .......................... 2013 1 0619979

(51) Int. Cl.
*A61B 5/00*    (2006.01)
*G06F 13/00*    (2006.01)
*G06F 11/30*    (2006.01)

(52) U.S. Cl.
CPC .............. *A61B 5/746* (2013.01); *G06F 11/30* (2013.01); *G06F 13/00* (2013.01)

(58) Field of Classification Search
None
See application file for complete search history.

(56) References Cited

U.S. PATENT DOCUMENTS 5,297,556 A * 3/1994 Shankar ............. A61B 5/02007
600/481
6,112,116 A * 8/2000 Fischell ............... A61N 1/3702
600/517

(Continued)

FOREIGN PATENT DOCUMENTS

| CN | 201662869 | 12/2010 |
|---|---|---|
| CN | 201804408 | 4/2011 |
| CN | 102821678 | 12/2012 |

OTHER PUBLICATIONS

International Search Report of PCT/CN2013/090292 dated Sep. 3, 2014, 4 pages (English and Chinese Translations).

*Primary Examiner* — Fekadeselassie Girma
(74) *Attorney, Agent, or Firm* — Rankin, Hill & Clark LLP

(57) ABSTRACT

Provided are a method of assisting monitoring alarm method and a medical external equipment and a medical host equipment using the method. A technical scheme thereof comprises connecting the medical external equipment with the medical host equipment through an interface, wherein the medical external equipment forms a plug-and-play external alarm equipment. The medical host equipment performs self-check, and sends an alarm information to an auxiliary alarm device of the medical external equipment and generates a corresponding alarm when an alarm device in the medical host equipment works abnormally, thereby reducing a risk to the medical host equipment in the situation that the alarm device in the medical host equipment is in failure.

14 Claims, 5 Drawing Sheets

(56) References Cited

U.S. PATENT DOCUMENTS

| | | | | |
|---|---|---|---|---|
| 6,272,379 | B1* | 8/2001 | Fischell | A61B 5/0031 |
| | | | | 600/515 |
| 7,292,141 | B2 | 11/2007 | Staats et al. | |
| 8,269,634 | B2 | 9/2012 | Fischell et al. | |
| 2004/0215254 | A1* | 10/2004 | Boute | A61B 5/0472 |
| | | | | 607/9 |
| 2005/0137530 | A1* | 6/2005 | Campbell | A61M 5/14244 |
| | | | | 604/131 |
| 2006/0064136 | A1* | 3/2006 | Wang | A61N 1/37258 |
| | | | | 607/27 |
| 2006/0074463 | A1* | 4/2006 | Seeberger | A61N 1/37252 |
| | | | | 607/60 |
| 2006/0235353 | A1* | 10/2006 | Gelfand | A61B 5/201 |
| | | | | 604/66 |
| 2006/0264777 | A1* | 11/2006 | Drew | A61B 5/048 |
| | | | | 600/547 |
| 2006/0265020 | A1* | 11/2006 | Fischell | A61N 1/37247 |
| | | | | 607/30 |
| 2006/0270971 | A1* | 11/2006 | Gelfand | A61B 5/201 |
| | | | | 604/66 |
| 2010/0198279 | A1* | 8/2010 | Corndorf | A61N 1/37276 |
| | | | | 607/3 |
| 2011/0241869 | A1* | 10/2011 | Kiani | A61B 5/1455 |
| | | | | 340/514 |
| 2012/0088983 | A1* | 4/2012 | Jung | G06F 3/014 |
| | | | | 600/301 |
| 2012/0271370 | A1* | 10/2012 | Hochhalter | A61N 1/37217 |
| | | | | 607/5 |

* cited by examiner

METHOD OF ASSISTING MONITORING ALARM AND MEDICAL EXTERNAL EQUIPMENT USING THE SAME

TECHNICAL FIELD

The present invention relates to the technical field of medical monitoring, in particular to a method of assisting monitoring alarm and a medical external equipment and a medical host equipment using the method.

BACKGROUND

Alarm function is very common and necessary in the medical field. Generally speaking, an alarm is a warning indicating that specific parameters of a patient monitored by a medical equipment exceeds a preset range of threshold, and the alarm has important significance in clinical practice and play an irreplaceable role in the procedure during which the medical staff timely obtain monitoring information and process it. The alarm for the central monitoring system generally makes use of a sound box, the sound box is connected to the host through a headphone jack, however the central monitoring system can't make the alarm if the sound box is not connected or in bad contact or in failure. If there is no alarm from the central monitoring system, the medical staff can't be aware of a variety of physiological alarms of the patients on different beds, then the medical staff can not perform treatment timely, which will cause significant damage on the patient's health and even life, and generate a significant risk and loss to the hospital and the patient. In addition, in the systems of various bed medical monitoring equipment, such as patient monitor, fetal monitor and so on, the alarm is the essential function, and a sound-light alarm is often used, if the device related to the alarm for medical equipment system is disconnected, connected poorly or malfunctions, the treatment can't be performed timely, which causes severe harm to the hospital and the patient. Therefore, the medical equipment system needs an effective method of assisting monitoring alarm, to avoid the existing defects in a condition of failure of the alarm device. Therefore, the existing technology has defects which need to be solved urgently.

SUMMARY

In order to overcome the defects mentioned above, the present invention aims at providing a method of assisting monitoring alarm and a medical external equipment and a medical host equipment using the method.

The purpose of the invention is realized through the following technical schemes:

A method of assisting monitoring alarm, comprising the following steps:

Step 1, starting up a medical equipment host system;

Step 2, judging whether there is an access from an external equipment by the medical equipment host system, if yes, going to step 3;

Step 3, reading a preset identity information of the external equipment and judging whether the accessing external equipment is the external equipment for assisting monitoring alarm by the medical equipment host system, if yes, going to step 4;

Step 4, checking whether an alarm device of the medical equipment host system is abnormal by the medical equipment host system, if is to step 5;

Step 5, sending an alarm level information to the external equipment for assisting monitoring alarm by the medical equipment host system;

Step 6, receiving the alarm level information and generating the corresponding alarm sound by the external equipment for assisting monitoring alarm.

Further more, the method further comprises the following steps after step 3:

Step 31, performing a self-check by the external equipment for assisting monitoring alarm;

Step 32, simultaneously generating a prompt sound and/or prompt light indicating that the self-check is passed by the external equipment for assisting monitoring alarm if the self-check is passed.

Further more, the method further comprises the following step after step 32: judging whether an information of activating a function of assisting alarm is received by the external equipment for assisting monitoring alarm.

Still further, the method further comprises the following step after step 3: judging whether an information of activating a function of assisting alarm is received by the external equipment for assisting monitoring alarm.

Still further, the preset identity information in step 3 comprises a protocol information and/or a manufacturer information and/or a serial number and/or an equipment identification.

Still further, the step 5 further comprises: sending an alarm type information to the external equipment for assisting monitoring alarm by the medical equipment host system.

Still further, the step 6 further comprises: receiving the alarm type information and generating the corresponding alarm sound and/or alarm light by the external equipment for assisting monitoring alarm.

A medical external equipment having a function of assisting monitoring alarm mentioned in the method mentioned above, comprising:

an external interface configured to connect with an medical equipment host system for intercommunication;

a power module connected with the external interface and configured to convert a voltage of the power supply from the external interface or provided by a DC power supply to the voltage suitable for the external equipment for assisting monitoring alarm;

a microprocessor connected to the external interface and the power module and configured to receive and process a communication information from the external interface;

an audio circuit connected to the power module and the microprocessor and configured to receive a control information from the microprocessor and perform audio decoding control and output; and a speaker connected with the audio circuit and configured to play an alarm prompt sound or play a self-check prompt sound.

Further more, the medical external equipment having the function of assisting monitoring alarm further comprises an LED module connected to the power module and the microprocessor and configured to receive the control information from the microprocessor and display alarm light or prompt light.

A medical host equipment having a function of assisting monitoring alarm mentioned in the method of claim 1, comprising:

an external interface connected with an external equipment for assisting monitoring alarm for intercommunication;

an external equipment access judgment module, connected with the external interface and configured to judge whether there is an access from the external equipment;

an external equipment matching judgment module, connected with the external interface and configured to judge whether the accessing external equipment is the external equipment for assisting monitoring alarm;

an alarm device status judgment module, connected with the external interface and configured to check whether an alarm device of the medical equipment host system is abnormal; and an alarm level information sending module, connected with the external interface and configured to send an alarm level information to the external equipment for assisting monitoring alarm.

The technical schemes of the present invention use methods for assisting alarm by using an external equipment and an equipment using the methods, which helps the medical monitoring equipment to carry out an auxiliary alarm. Through a plug-and-play external alarm equipment, a software is designed according to a protocol developed by the external alarm equipment, the medical equipment system detects whether a alarm device thereof is abnormal, if yes, the external alarm equipment of the present invention may be used for alarm, which reduces the risk to the medical equipment system in the situation that the alarm device thereof is in failure. The equipment of the present invention can use various kinds of existing external interfaces, such as: USB interface, serial port, parallel port, PS2, network interface etc., and is connected with the central monitoring system.

BRIEF DESCRIPTION OF THE DRAWINGS

For ease of illustration, the present invention is described in detail by the following preferred embodiments and the accompanying drawings.

DESCRIPTION OF EMBODIMENTS

To make the objectives, technical solutions, and advantages of the present invention clearer, the following further describes the present invention in detail with reference to the accompanying drawings and embodiments.

Figure 1:
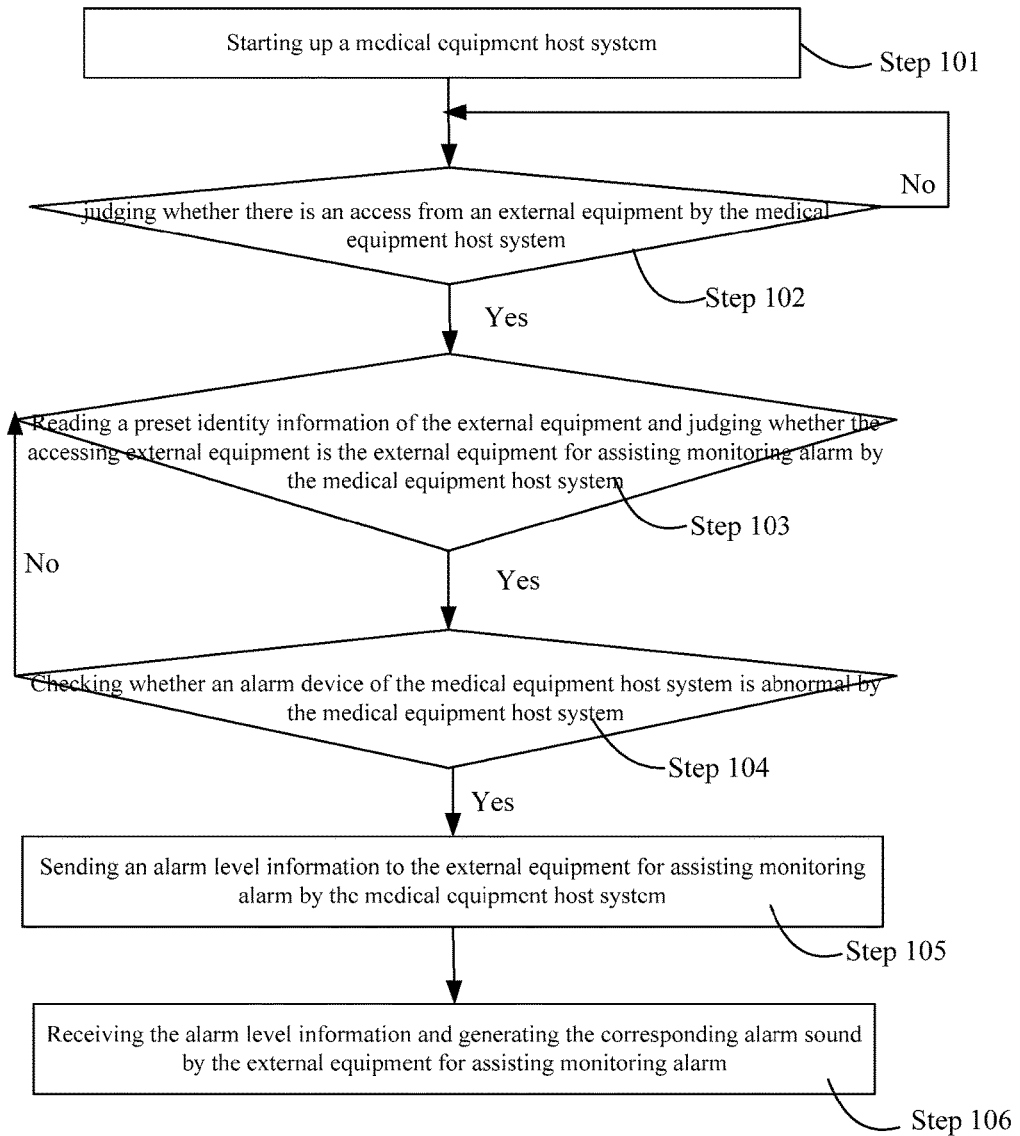
FIG. 1 is a schematic flowchart of one embodiment of the method of assisting monitoring alarm of the present invention.

As shown in FIG. 1, the method of assisting monitoring alarm of the present invention comprises the following steps:

step 101, starting up a medical equipment host system;

wherein the medical equipment system may be a central monitoring system, a bedside monitoring equipment, and so on, the medical equipment system implemented by an software follows a communication protocol developed by an external alarm monitoring equipment, and the external alarm monitoring equipment may be used to makes a sound alarm, or make a sound and light alarm for the system, step 102, judging whether there is an access from an external equipment by the medical equipment host system;

wherein, after started up, the medical equipment system detects whether there is an access from an external equipment for assisting monitoring alarm at a specific external interface, the medical equipment system scans the external interface of the equipment at a certain interval to detect the access of the external equipment for assisting monitoring alarm; if the access from an external equipment is detected, the detection is stopped. If there is no access from the equipment, the detection continues, that is, this step is repeated;

step 103, reading a preset identity information of the external equipment and judging whether the accessing external equipment is the external equipment for assisting monitoring alarm by the medical equipment host system;

wherein when the medical equipment system scans and find the access from the external equipment, the medical equipment system judges whether the external equipment is matched; the detection method may comprise: reading some preset information of the equipment, such as protocol information, manufacturer information, serial number, equipment identification, etc.; if the equipment is matched, the detection is passed and the equipment is judged as the external equipment for assisting monitoring alarm; if the equipment is not matched, the step 102 is repeated;

step 104, checking whether an alarm device of the medical equipment host system is abnormal by the medical equipment host system;

wherein after the started, when having detected the access from the external equipment for assisting monitoring alarm, the medical equipment system continuously checks whether the alarm device of the medical equipment host system is abnormal at a certain interval; if the alarm device works normally, step 104 is repeated to continue the detection; if the alarm device works abnormally, the step 105 is entered, that is the external equipment for assisting monitoring alarm is used to make alarm, the alarm device of the medical equipment host system may be an external sound box, for example the central monitoring system uses an external sound box to make alarm, or a built-in alarm speaker in the medical equipment system, by detecting whether the alarm device of the medical equipment system is abnormal, the method may judge whether the external equipment for assisting monitoring alarm is used to make alarm, the alarm device of the medical equipment system works abnormally may be caused by disconnection, poor contact, or failure of the alarm device, such as the failure of a speaker or the failure of a driving circuit, in general, by detecting the voltage or current, the disconnection, poor contact, or failure of the alarm device may be determined;

step 105, sending an alarm level information to the external equipment for assisting monitoring alarm by the medical equipment host system;

wherein when the alarm device of the medical equipment host system is abnormal, the external equipment for assisting monitoring alarm is used to make alarm, the medical equipment system monitors various physiological parameters of the patients, if the physiological parameters of the patient monitored exceeds the preset threshold, the external equipment for assisting monitoring alarm makes alarm; the medical equipment system generates different alarm sounds according to alarm content, the alarm sounds are classified into various categories: senior alarm sound, intermediate alarm sound and low alarm sound, according to an alarm sound information, the medical equipment system sends a preset alarm level information to the external equipment for assisting monitoring alarm, the content of the predetermined alarm level information as specific implementation are as follows:

TABLE 1 the predetermined alarm level information sent by the medical equipment system

| Byte | Content | Meaning | The number of byte occupied |
|---|---|---|---|
| byte 0 | 0xFF | Packet header | 1 |
| byte 1 | 8 (decimal) | Packet length | 1 |
| byte 2 | 0x01 | Module identification code | 1 |
| byte 3 | 0x05 | Frame type | 1 |
| byte 4 + 0 | *** | Zeroth byte of alarm level | 4 |
| byte 4 + 1 | *** | First byte of alarm level | |
| byte 8 | *** | High byte of checksum | 1 |
| byte 9 | *** | Low byte of checksum | 1 |

Note:
the alarm level only occupies the zeroth byte, and the first byte is reserved. For the values of the zeroth bytes, the values of the sound alarms are as follow: the value of the low level alarm is 0x10, the value of the intermediate alarm is 0x20, and the value of the senior alarm is 0x30.
Note:
Checksum = sum of the values from byte (2) to byte (4);
High byte of checksum = (Checksum & 0xFF0) >> 8;
Low byte of checksum = (Checksum & 0x00FF)
Packet length = the total number of bytes from module identification code (byte3) to low byte of checksum (byte (N + 6)).

step 106, receiving the alarm level information and generating the corresponding alarm sound by the external equipment for assisting monitoring alarm;

wherein the external equipment for assisting monitoring alarm receives the alarm level information sent by the medical system, and makes corresponding sound alarm according to the content of the information after receiving the alarm level informatinon, the alarm sounds are classified into: low level alarm, intermediate alarm and senior alarm.

To make the objectives, technical solutions, and advantages of the present invention clearer, the following further describes the present invention in detail with reference to the accompanying drawings and embodiments. Another embodiment of the method of assisting monitoring alarm of the present invention is provided.

Figure 2:
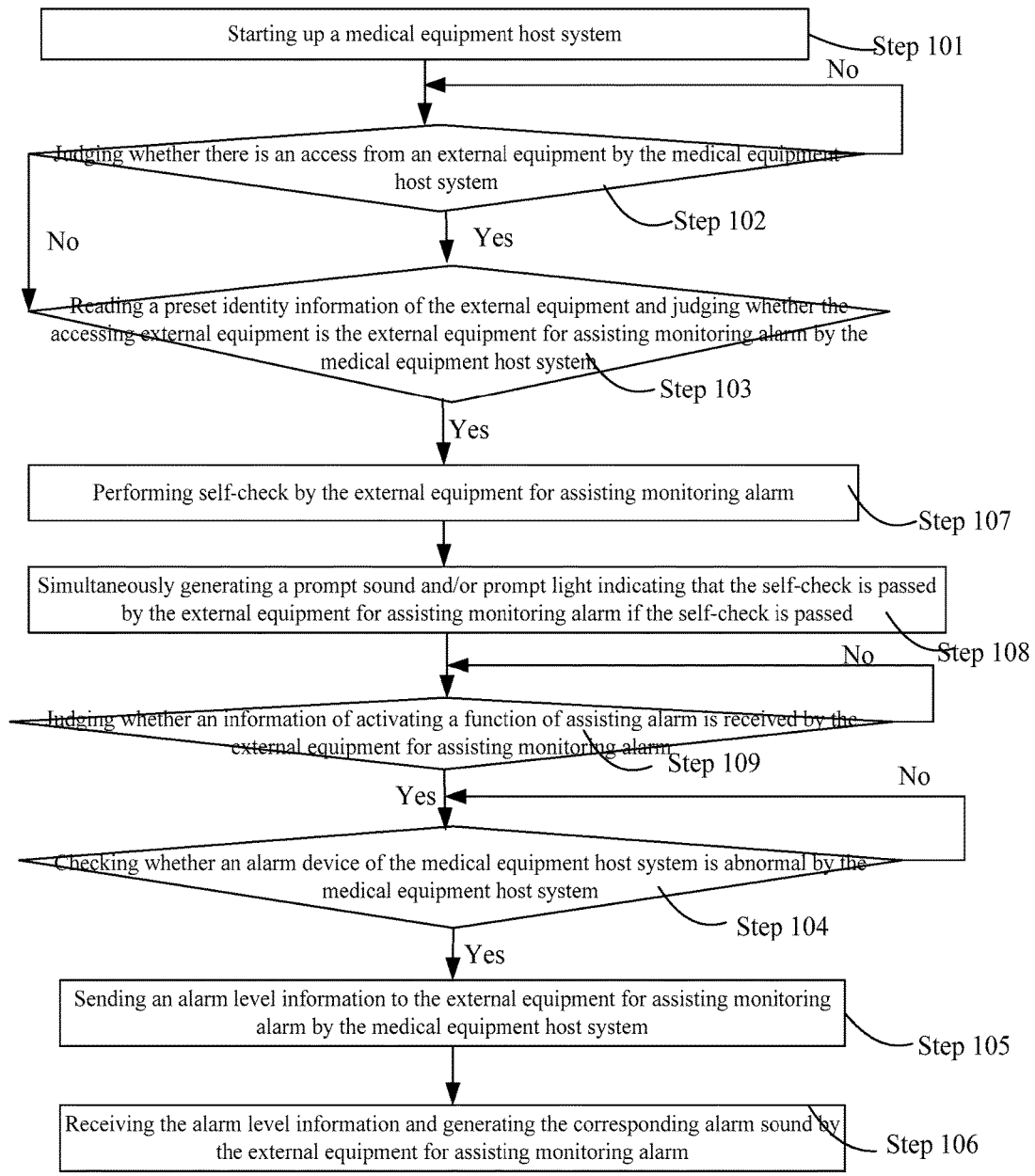
FIG. 2 is a schematic flowchart of another embodiment of the method of assisting monitoring alarm of the present invention.

As shown in FIG. 2, the specific steps of another embodiment of the method of assisting monitoring alarm of the present invention are described as follow:

After the step 103, the method further comprises:

step 107, performing self-check by the external equipment for assisting monitoring alarm;

when the external equipment for assisting monitoring alarm accesses medical equipment system, the external equipment for assisting monitoring alarm performs self-check, to detect whether the program and the hardware of the external equipment for assisting monitoring alarm work normally, step 108, simultaneously generating a prompt sound and/ or prompt light indicating that the self-check is passed by the external equipment for assisting monitoring alarm if the self-check is passed;

It means that the external equipment for assisting monitoring alarm works normally, the user can easily know the working status of the external equipment for assisting monitoring alarm.

After step 108, the method may go directly to step 104 (not shown) or to step 109.

Figure 3:
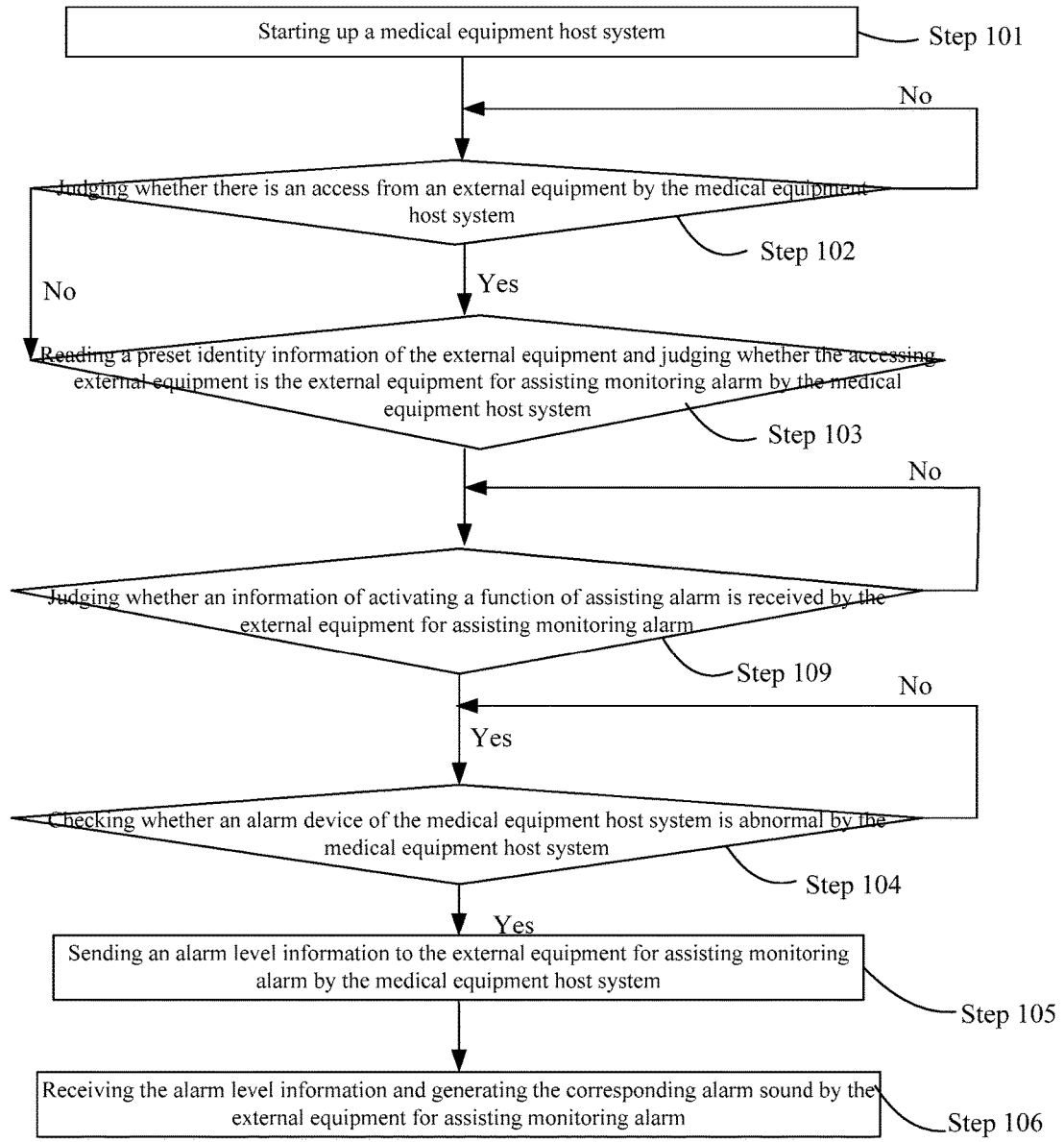
FIG. 3 is a schematic flowchart of a third embodiment of the method of assisting monitoring alarm of the present invention.

As shown in FIGS. 2 and 3, after the step 103 or the step 108, the method further comprises: step 109, judging whether an information of activating a function of assisting alarm is received by the external equipment for assisting monitoring al arm.

The medical equipment system may send an activating information to control whether the external equipment for assisting monitoring alarm activates the function of assisting alarm. The external equipment for assisting monitoring alarm activates the function of assisting alarm when receives the activating information; if no activating information is received, the step is repeated. Generally speaking, for integration of resources utilization, the external equipment for assisting monitoring alarm has encryption dog, storage and other functions. By switching on a switch to control the function of assisting alarm, users can easily choose whether the function of assisting alarm is needed, thereby using the resources reasonably.

The content of the information of activating the function of assisting alarm as specific implementation are as follows:

TABLE 2 medical equipment system sends the information of activating the function of assisting alarm

| Byte | Content | Meaning | The number of byte occupied |
|---|---|---|---|
| byte 0 | 0xFF | Packet header | 1 |
| byte 1 | 5 (decimal) | Packet length | 1 |
| byte 2 | 0x01 | Module identification code | 1 |
| byte 3 | 0x08 | Frame type | 1 |
| byte 4 | *** | 0x01: switch on 0x00: switch off | 1 |
| byte 5 | *** | High byte of checksum | 1 |
| byte 6 | *** | Low byte of checksum | 1 |

Note:
Checksum = sum of the values from byte (2) to byte (4 + N);
High byte of checksum = (Checksum & 0xFF00) >> 8;
Low byte of checksum = (Checksum & 0x00FF)
Packet length = the total number of bytes from module identification code (byte3) to low byte of checksum (byte (N + 6))

In the step 104 of checking whether an alarm device of the medical equipment host system is abnormal, preferably the alarm device may not only be the sound alarm device, but also be alarm lamp in the medical equipment system, such as alarm lamp of a monitor. Checking whether the alarm device of the medical equipment system alarm is abnormal may determine whether it needs to use the external alarm monitoring equipment to make light alarm. The alarm device of the medical equipment system works abnormally may be caused by disconnection, poor contact, or failure of the alarm device, such as the failure of a speaker or the failure of a driving circuit. In general, by detecting the voltage or current, the disconnection, poor contact, or failure of the alarm device may be determined.

In the step 105, in addition to sending alarm level information, preferably the medical equipment host system may also send an alarm type information to the external equipment for assisting monitoring alarm;

If the alarm device of the medical equipment system host is abnormal, the external equipment for assisting monitoring alarm is used to make alarm, the medical equipment system monitors various physiological parameters of the patients, if the physiological parameters of the patient monitored exceeds the preset threshold, the external equipment for assisting monitoring alarm makes alarm; the medical equipment system generates different alarm sounds and alarm lights according to alarm content, the alarm lights are classified into various categories: senior alarm light, intermediate alarm light and low alarm light (in general, at the lower and intermediate level the yellow lamp flashes, at senior level the red lamp flashes). According to an alarm light information, the medical equipment system sends preset alarm level information and type information to the external equipment for assisting monitoring alarm. The content of the preset alarm level information and type information as specific implementation are as follows:

The medical equipment system to send preset alarm level information and type information

| Byte | Content | Meaning | The number of byte occupied |
|---|---|---|---|
| byte 0 | 0xFF | Packet header | 1 |
| byte 1 | 8 (decimal) | Packet length | 1 |
| byte 2 | 0x01 | Module identification code | 1 |
| byte 3 | 0x05 | Frame type | 1 |
| byte 4 + 0 | *** | Zeroth byte of alarm type | 4 |
| byte 4 + 1 | *** | First byte of alarm level | |
| byte 4 + 2 | *** | Zeroth byte of alarm type | 1 |
| byte 4 + 3 | *** | First byte of alarm level | 1 |
| byte 8 | *** | High byte of checksum | |
| byte 9 | *** | Low byte of checksum | |

Note:
the zeroth byte of the two bytes for alarm classification is used, and the first byte is reserved. For the values of the zeroth bytes, the value of the sound alarms is 0x10, the value of the light alarm is 0x20; the alarm level only occupies the zeroth byte, and the first byte is reserved. For the values of the zeroth bytes, the values of the sound alarms are as follow: the value of the low level alarm is 0x10, the value of the intermediate alarm is 0x20, and the value of the senior alarm is 0x30. The values of the light alarms are as follow: the value of the low level alarm is 0x10, the value of the intermediate alarm is 0x20, and the value of the senior alarm is 0x30.

Note:
Checksum = sum of the values from byte (2) to byte (4 + N);
High byte of checksum = (Checksum & 0xFF00) >>8;
Low byte of checksum = (Checksum & 0x00FF)
Packet length = the total number of bytes from module identification code (byte3) to low byte of checksum (byte (N + 6)).

Correspondingly, the step 106 of receiving the alarm level information and generating the corresponding alarm sound by the external equipment for assisting monitoring alarm preferably comprises: receiving the alarm type information and generating the corresponding alarm sound and/or alarm light by the external equipment for assisting monitoring alarm;

To make the objectives, technical solutions, and advantages of the present invention clearer, the following further describes the present invention in detail with reference to the accompanying drawings and embodiments.

Figure 4:
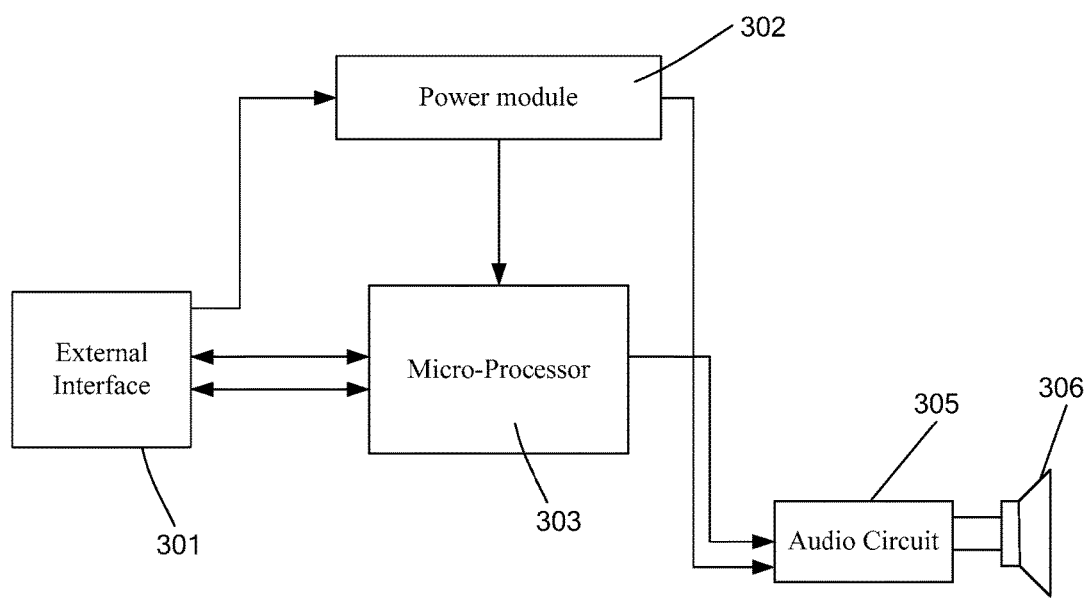
FIG. 4 is a schematic circuit of the medical external equipment having a function of assisting monitoring alarm of the present invention.

As shown in FIG. 4, the schematic circuit of the medical external equipment having a function of assisting monitoring alarm of the present invention is described as follow, the medical external equipment comprises:

an external interface 301, configured to connect with an medical equipment host system for intercommunication;

wherein the general external interface of the external equipment for assisting monitoring alarm (such as USB port, serial port, parallel port, PS2, Ethernet port and so on), is connected to the medical equipment system through the external interface 301, the external equipment for assisting monitoring alarm may obtain power required by the external equipment for assisting monitoring alarm through the external interface 301, and the external equipment fir assisting monitoring alarm may communicate with the medical equipment system through the external interface 301;

a power module 302, connected with the external interface and configured to convert a voltage of the power supply from the external interface or provided by a DC power supply to the voltage suitable for the external equipment for assisting monitoring alarm;

wherein the power module is connected to the external interface, a microprocessor and an audio circuit, the power module converts a voltage of the power supply from the external interface or provided by a DC power supply to the voltage suitable for different devices, and some interfaces that can't provide power may use the DC power supply such as a battery to provide power to the processor and the audio circuit module by converting the voltage to the required voltage by the power module;

a microprocessor 303, connected to the external interface 301 and the power module 302 and configured to receive and process a communication information from the external interface;

wherein the microprocessor is configured to receive the communication information, perform self-check to the external equipment for assisting monitoring alarm and control the output of the audio and light signals;

an audio circuit 305, connected to the power module 302 and the microprocessor 303 and configured to receive a control information from the microprocessor and perform audio decoding control and output; and a speaker 306, connected with the audio circuit 305 and configured to play an alarm prompt sound or play a self-check prompt sound.

Figure 5:
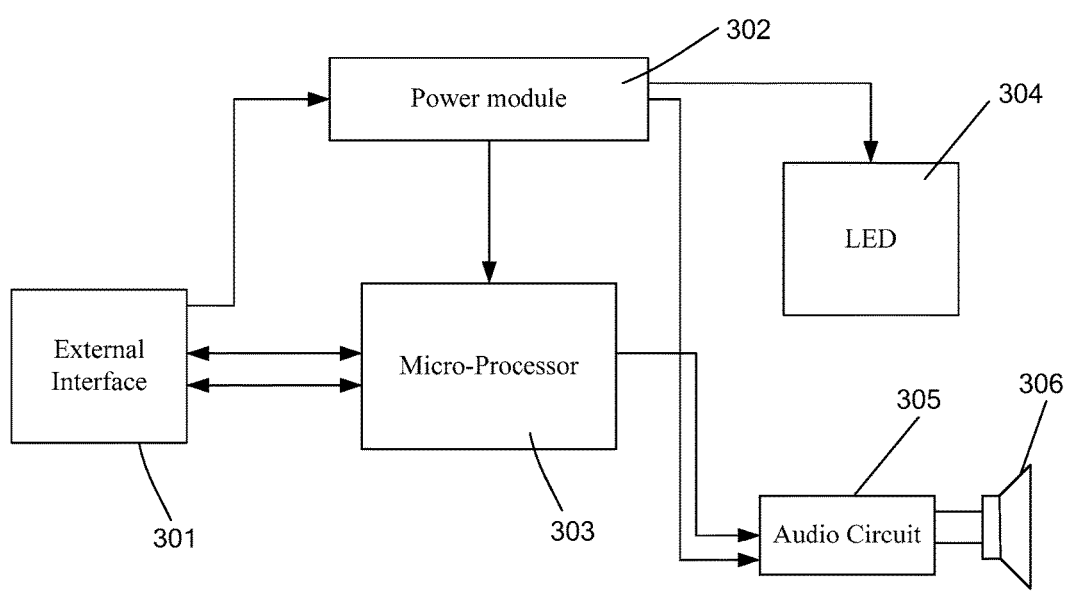
FIG. 5 is an another schematic circuit of the medical external equipment having a function of assisting monitoring alarm of the present invention.

As shown in FIG. 5, another schematic circuit of the medical external equipment having a function of assisting monitoring alarm of the present invention is described as follow, the medical external equipment further comprises:

an LED module 304, connected to the power module 302 and the microprocessor 303 and configured to receive the control information from the microprocessor and display alarm light or prompt light.

In addition, in order to explain the invention better, the invention also provides a medical host equipment having a function of assisting monitoring alarm comprising:

an external interface connected with an external equipment for assisting monitoring alarm for intercommunication;

an external equipment access judgment module, connected with the external interface and configured to judge whether there is an access from the external equipment;

an external equipment matching judgment module, connected with the external interface and configured to judge whether the accessing external equipment is the external equipment for assisting monitoring alarm;

an alarm device status judgment module, connected with the external interface and to check whether an alarm device of the medical equipment host system is abnormal; and an alarm level information sending module, connected with the external interface and configured to send an alarm level information to the external equipment for assisting monitoring alarm.

Further, the medical host equipment also has a software crash monitoring function, and further comprises:

an alarm-assisting activating module, connected with the external interface and configure to activate communication information of assisting alarm; and a alarm type information sending module, connected with the external interface and configured to send the alarm type information to the external equipment for assisting monitoring alarm.

The foregoing descriptions are merely exemplary embodiment of the present invention, but are not intended to limit the present invention to it. Any modification, equivalent replacement, or improvement made without departing from the spirit and principle of the present invention shall fall within the protection scope of the present invention.

What is claimed is:

1. A method of assisting monitoring alarm in a medical equipment host system consisting of a medical host equipment and a medical external equipment, comprising the following steps:
   Step 1, starting up the medical equipment host system;
   Step 2, judging whether there is an access from an external equipment by an external equipment access judgment module of the medical host equipment of the medical equipment host system, if yes, going to step 3;
   Step 3, reading a preset identity information of the external equipment and judging whether the accessing external equipment is the external equipment for assisting monitoring alarm by an external equipment matching judgment module of the medical host equipment of the medical equipment host system, if yes, going to step 4;
   Step 4, checking whether an alarm device of the medical host equipment of the medical equipment host system is abnormal by an alarm device status judgment module of the medical host equipment of the medical equipment host system, if is to step 5;
   Step 5, sending an alarm level information to the external equipment for assisting monitoring alarm by an alarm level information sending module of the medical host equipment of the medical equipment host system;
   Step 6, receiving the alarm level information and generating the corresponding alarm sound by an external interface of the external equipment for assisting monitoring alarm, wherein the external interface of the external equipment is configured to connect with the medical equipment host system for intercommunication.

2. The method of claim 1, wherein the method further comprises the following steps after step 3:
   Step 31, performing a self-check by the external equipment for assisting monitoring alarm;
   Step 32, simultaneously generating a prompt sound by an audio circuit and/or prompt light by an LED module indicating that the self-check is passed by the external equipment for assisting monitoring alarm if the self-check is passed.

3. The method of claim 2, the method further comprises the following step after step 32: by the medical host equipment of the medical equipment host system, judging whether an information of activating a function of assisting alarm is received by the external equipment for assisting monitoring alarm.

4. The method of claim 1, wherein the method further comprises the following step after step 3: by the medical host equipment of the medical equipment host system, judging whether an information of activating a function of assisting alarm is received by the external equipment for assisting monitoring alarm.

5. The method of claim 1, wherein the preset identity information in step 3 comprises a protocol information and/or a manufacturer information and/or a serial number and/or an equipment identification.

6. The method of claim 1, wherein the step 5 further comprises: by an alarm level information sending module of the medical host equipment of the medical equipment host system, sending an alarm type information to the external equipment for assisting monitoring alarm by the medical equipment host system.

7. The method of claim 1, wherein the step 6 further comprises: receiving the alarm type information and generating the corresponding alarm sound and/or alarm light by the external equipment for assisting monitoring alarm.

8. A medical external equipment having a function of assisting monitoring alarm mentioned in the method of claim 1, comprising:
   an external interface configured to connect with an medical equipment host system for intercommunication;
   a power module connected with the external interface and configured to convert a voltage of the power supply from the external interface or provided by a DC power supply to the voltage suitable for the external equipment for assisting monitoring alarm;
   a microprocessor connected to the external interface and the power module and configured to receive and process a communication information from the external interface;
   an audio circuit connected to the power module and the microprocessor and configured to receive a control information from the microprocessor and perform audio decoding control and output; and
   a speaker connected with the audio circuit and configured to play an alarm prompt sound or play a self-check prompt sound.

9. The medical external equipment having the function of assisting monitoring alarm of claim 8, further comprises an LED module connected to the power module and the microprocessor and configured to receive the control information from the microprocessor and display alarm light or prompt light.

10. A medical host equipment having a function of assisting monitoring alarm mentioned in the method of claim 1, comprising:
   an external interface connected with an external equipment for assisting monitoring alarm for intercommunication;
   an external equipment access judgment module connected with the external interface and configured to judge whether there is an access from the external equipment;
   an external equipment matching judgment module connected with the external interface and configured to judge whether the accessing external equipment is the external equipment for assisting monitoring alarm;
   an alarm device status judgment module connected with the external interface and configured to check whether an alarm device of the medical equipment host system is abnormal; and
   an alarm level information sending module connected with the external interface and configured to send an alarm level information to the external equipment for assisting monitoring alarm.

11. The method of assisting monitoring alarm according to claim 1, judging whether there is an access from an external equipment by the external equipment access judgment module of the medical host equipment of the medical equipment host system specifically comprises:
   by the external equipment access judgment module of the medical equipment host system, scanning the external interface of the medical equipment host system at a certain interval to detect the access of the external equipment for assisting monitoring alarm; if the access from the external equipment is detected, the detection is stopped; if there is no access from the external equipment, repeatedly executing step 3.

12. The method of assisting monitoring alarm according to claim 1, wherein checking whether an alarm device of the medical host equipment of the medical equipment host system is abnormal by the alarm device status judgment module of the medical host equipment of the medical equipment host system specifically comprises:
   when the access from the external equipment for assisting monitoring alarm has been detected by the external equipment access judgment module of the medical host equipment, continuously checking whether the alarm device of the medical equipment host system is abnormal at a certain interval by the alarm device status judgment module of the medical host equipment.

13. The method of assisting monitoring alarm according to claim 1, wherein the alarming device is an alarm lamp in the medical equipment host system, the method of assisting monitoring alarm further comprises:
   by the alarm device status judgment module of the medical host equipment, determining whether it needs to use the external equipment to make a light alarm by checking whether the alarm device of the medical equipment host system is abnormal.

14. The medical host equipment having a function of assisting monitoring alarm according to claim 10, further comprising:
   an alarm-assisting activating module connected with the external interface and configured to activate communication information of assisting alarm; and
   an alarm type information sending module connected with the external interface and configured to send the alarm type information to the external equipment for assisting monitoring alarm.

\* \* \* \* \*